United States Patent
Kawaguchi

(10) Patent No.: US 8,077,306 B2
(45) Date of Patent: Dec. 13, 2011

(54) DEFECT INSPECTION APPARATUS

(75) Inventor: Hiroshi Kawaguchi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 701 days.

(21) Appl. No.: 11/844,452

(22) Filed: Aug. 24, 2007

(65) Prior Publication Data
US 2008/0055600 A1 Mar. 6, 2008

(30) Foreign Application Priority Data

Aug. 25, 2006 (JP) ................................. 2006-228545
Jan. 31, 2007 (JP) ................................. 2007-020789

(51) Int. Cl.
*G01N 21/00* (2006.01)
(52) U.S. Cl. ..................................................... 356/237.1
(58) Field of Classification Search .................. None
See application file for complete search history.

(56) References Cited

U.S. PATENT DOCUMENTS

| | | | | | |
|---|---|---|---|---|---|
| 4,602,289 | A * | 7/1986 | Sekine | ........................ | 250/208.1 |
| 4,853,970 | A * | 8/1989 | Ott et al. | ........................ | 382/266 |
| 5,130,814 | A * | 7/1992 | Spencer | ........................ | 386/109 |
| 5,264,694 | A * | 11/1993 | Diehl et al. | ................ | 250/208.1 |
| 5,488,239 | A * | 1/1996 | Jung | ............................... | 257/231 |
| 5,940,173 | A * | 8/1999 | Tomii et al. | ................... | 356/445 |
| 6,166,831 | A * | 12/2000 | Boyd et al. | .................... | 358/483 |
| 6,456,793 | B1 * | 9/2002 | Ray et al. | ........................ | 396/89 |
| 6,471,916 | B1 * | 10/2002 | Noblett | .......................... | 356/317 |
| 6,724,473 | B2 * | 4/2004 | Leong et al. | ................ | 356/237.2 |
| 7,045,758 | B2 * | 5/2006 | Zarnowski et al. | ........ | 250/208.1 |
| 7,173,658 | B2 * | 2/2007 | Kikuchi | ......................... | 348/275 |
| 7,355,690 | B2 * | 4/2008 | Elyasaf et al. | ............. | 356/237.2 |
| 7,388,979 | B2 * | 6/2008 | Sakai et al. | ................. | 356/237.4 |
| 7,479,642 | B2 * | 1/2009 | Maack | .......................... | 250/394 |
| 2002/0191828 | A1 * | 12/2002 | Colbeth et al. | ................ | 382/132 |

FOREIGN PATENT DOCUMENTS

| | | |
|---|---|---|
| JP | 5-182887 | 7/1993 |
| JP | 2000-97869 A | 4/2000 |
| JP | 2000-311926 A | 11/2000 |
| JP | 2001-201461 A | 7/2001 |
| JP | 2001-25429 A | 8/2001 |
| JP | 2002-310932 A | 10/2002 |
| JP | 2006-201044 A | 8/2006 |
| WO | 3-110454 A | 5/1991 |
| WO | 9-210793 A | 8/1997 |
| WO | 2005/026782 A2 | 3/2005 |

* cited by examiner

*Primary Examiner* — Michael A Lyons
*Assistant Examiner* — Juan D Valentin
(74) *Attorney, Agent, or Firm* — Mattingly & Malur, P.C.

(57) ABSTRACT

A high speed defect inspection apparatus has a high-speed detector that includes a plurality of image sensors. The image sensors are arranged with gaps between them in the pixel direction to form two lines. The image sensors are arranged in a zigzag pattern so that they are not contiguous to each other in the scanning direction. The development cost is reduced by using an arrangement of a plurality of small-area image sensors. When an image sensor is installed, it is necessary to furnish a region required for installation. Since individual image sensors need to be arranged at fixed intervals, void regions result. A plurality of image sensors are arranged in a zigzag pattern to solve the void region problem.

20 Claims, 7 Drawing Sheets

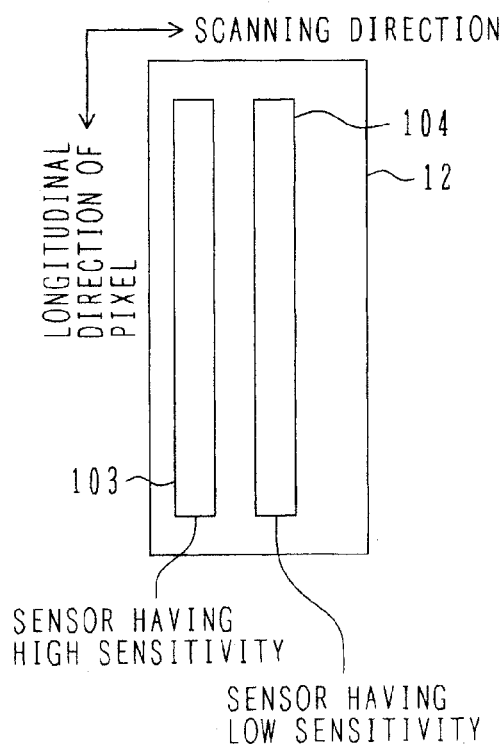
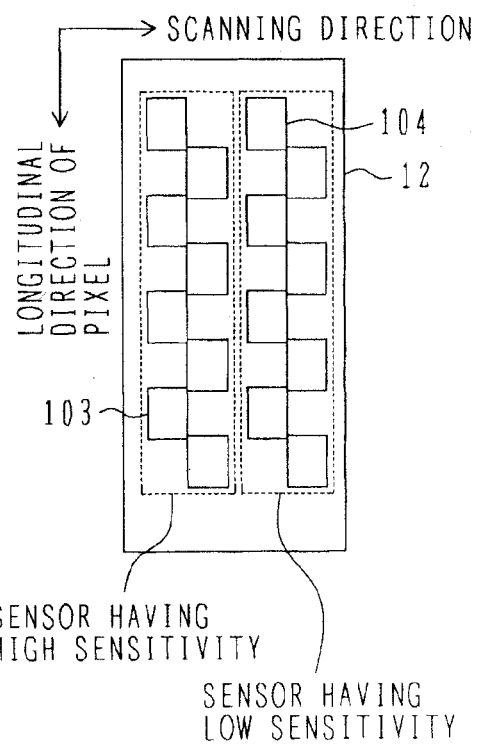
FIG. 6A
FIG. 6B

DEFECT INSPECTION APPARATUS

BACKGROUND OF THE INVENTION

1. Field of the Invention

The present invention relates to a defect inspection apparatus that detects defects (e.g., shorts and wire breaks) and foreign matter in an inspection target pattern, and more particularly to a defect inspection apparatus that includes a plurality of photoelectric image sensors as a detector.

2. Description of the Related Art

In general, conventional methods for raising the inspection speed of a defect inspection apparatus have been used to increase the speed of an image sensor, which is employed as a detector. For example, the speed of an image sensor has been increased by the use of a method that divides the output of an image sensor having a large inspection field of view or a large number of pixels into even-numbered pixels and odd-numbered pixels and output the resulting pixels in a parallel manner or by the use of a so-called multi-tap output method, which divides all pixels of an image sensor into a plurality of groups and outputs them in a parallel manner.

A known inspection apparatus disclosed, for instance, by JP-A-5-182887 uses a photoelectric image sensor as a detector. An inspection apparatus like this one uses a detector that includes a one- or two-dimensional array of photoelectric image sensors.

SUMMARY OF THE INVENTION

The most effective method of raising the inspection speed of an image-sensor-based inspection apparatus is to increase the operating speed of an image sensor having a large number of pixels, for instance, by generating image sensor outputs in a parallel manner.

However, the production of an image sensor having a large number of pixels requires a huge development cost and a long development period. Since a large number of pixels are involved, it is anticipated, for instance, that the yield rate may decrease due to an increase in the frequency of pixel defect occurrence during the manufacture of a large-area image sensor.

To solve the above problem, it is an object of the present invention to raise the inspection speed of a defect inspection apparatus by providing a high-speed detector without requiring a huge development cost or a long development period and without lowering the yield rate.

According to one aspect of the present invention, there is provided a defect inspection apparatus including: illumination unit for illuminating an inspection target; a detector for receiving light reflected from the inspection target; transport unit for transporting the detector or a stage on which the inspection target is mounted; and inspection unit for inspecting the inspection target in accordance with an image detected by the detector. The detector includes a plurality of photoelectric image sensors, which are alternately arranged in each of two or more lines to form a lattice-like pattern.

The present invention makes it possible to raise the inspection speed of a defect inspection apparatus by providing a high-speed detector without requiring a huge development cost or a long development period and without lowering the yield rate.

BRIEF DESCRIPTION OF THE DRAWINGS

FIGS. 6A and 6B show typical detector configurations in which image sensors having different sensitivities are arranged to form a plurality of lines within the defect inspection apparatus according to the present invention.

DETAILED DESCRIPTION OF THE PREFERRED EMBODIMENTS

Embodiments of the present invention will now be described with reference to the accompanying drawings.

Figure 1:
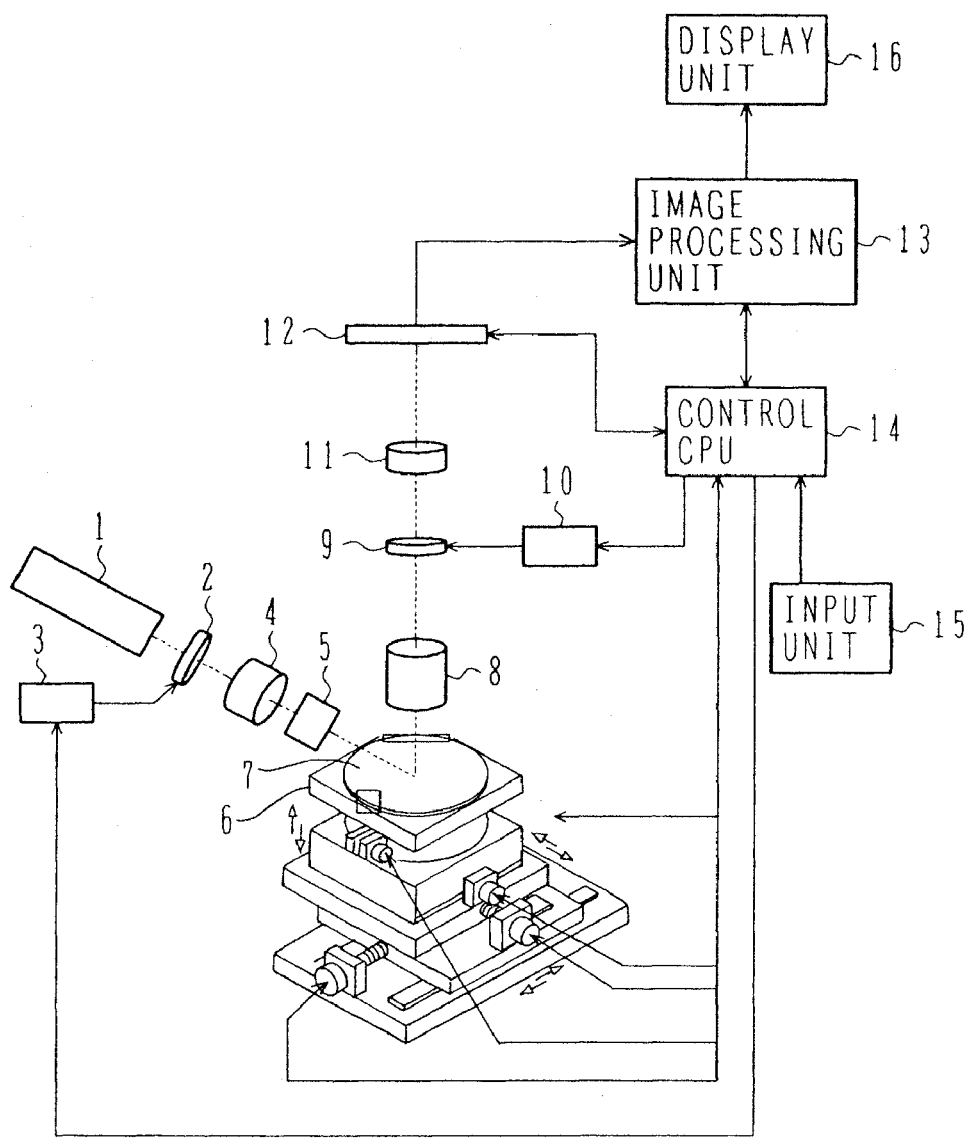
FIG. 1 shows a defect inspection apparatus according to an embodiment of the present invention.

FIG. 1 is a schematic diagram illustrating the configuration of a defect inspection apparatus to which the present invention is applied. Referring to FIG. 1, a stage includes X, Y, Z, and θ (rotation) stages. A semiconductor wafer (specimen) 7, which is a typical inspection target pattern, is to be mounted on the stage 6. An illumination light source 1 is made of an ultraviolet or far-ultraviolet laser light source having a wavelength of 266 nm or 355 nm and used to illuminate the specimen 7.

The ultraviolet laser light source includes a device that uses a nonlinear optical crystal or the like, subjects a solid YAG laser to wavelength conversion, and generates a third harmonic (355 nm) or fourth harmonic (266 nm) of a fundamental wave. Alternatively, a laser light source having a wavelength of 193 nm, 195 nm, or 248 nm may be used. Another alternative is to use a laser light source having a wavelength of 100 nm or less if such exists. The use of such a laser light source would provide increased resolution.

Either continuous oscillation or pulsed oscillation may be employed as the form of laser oscillation. However, the use of continuous oscillation is preferred because an image of the inspection target 7 is to be detected while the stage continuously travels. A control CPU 14 controls the stage 6 in a manner not shown so that the stage 6 moves in X, Y, Z, or θ direction.

The illumination light emitted from the light source 1 is controlled by an ND filter 2, which limits the amount of light, so that the amount of light required for inspection is obtained. The ND filter 2 can be driven in a manner not shown but in accordance with instructions from an ND filter control circuit 3. A beam expander 4 enlarges a beam of light that is emitted from the light source 1. The enlarged light beam obliquely falls on the specimen 7 to provide dark-field illumination while the illumination area of the specimen 7 mounted on the stage 6 is set by an illumination optics 5.

Scattered light reflected from the specimen 7 travels, for instance, through an objective lens 8, a spatial filter 9, and an imaging lens 11, and is detected by a detector (defect detector) 12. The detected light is subjected, for instance, to binarization in an image processing unit 13 for defect detection purposes. The spatial filter 9 can be driven in a manner not shown but in accordance with instructions from a spatial filter control circuit 10. This filter 9 can block diffracted light from a repetitive pattern on the specimen 7.

A display unit 16 displays, for instance, image processing results. The control CPU 14 controls the information input from an input unit 15 and the data and information of the image processing unit 13, detector 12, and stage 6.

The detector 12 includes a plurality of image sensors that are arranged in a lattice pattern.

FIGS. 2A to 2D show typical detector configurations that may be employed when line sensors are used with the defect inspection apparatus according to the present invention. The detector 12 includes a plurality of image sensors 100. The plurality of image sensors 100 (four image sensors in the examples shown in the figures) are arranged at certain intervals in a pixel direction (in a direction perpendicular to a scanning direction). The image sensors 100 are arranged in the above manner to form two lines. Further, the image sensors 100 are arranged so that they are not contiguous to each other in the scanning direction (in a direction in which the inspection target is scanned). In other words, the plurality of image sensors 100 are arranged in a zigzag pattern.

As mentioned earlier, the production of a large-area image sensor having a large number of pixels requires a huge development cost and a long development period. Since a large number of pixels are involved, the frequency of pixel defect occurrence increases.

To avoid the above problem, an embodiment of the present invention adopts an arrangement of a plurality of small-area image sensors. When an image sensor is to be installed, it is necessary to furnish a region required for installation. Individual image sensors need to be arranged at fixed intervals. Consequently, void regions result.

To solve the above void region problem, an embodiment of the present invention arranges the plurality of image sensors in a zigzag pattern.

As a result, the present invention makes it possible to implement a high-speed detector without requiring a huge development cost or a long development period and without lowering the yield rate.

Figure 2A:
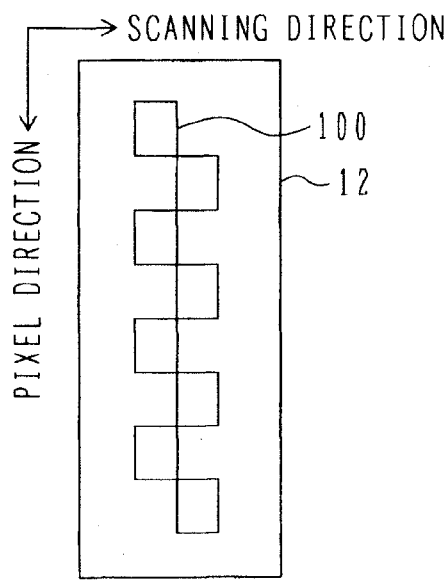
FIGS. 2A to 2D show typical detector configurations that may be employed when line sensors are used with the defect inspection apparatus according to the present invention.

In an arrangement example shown in FIG. 2A, the image sensors 100 are arranged with no gaps between them in both the pixel direction and scanning direction. In an example shown in FIG. 2B, the image sensors 100 are arranged with gaps between them in the scanning direction.

Figure 2B:
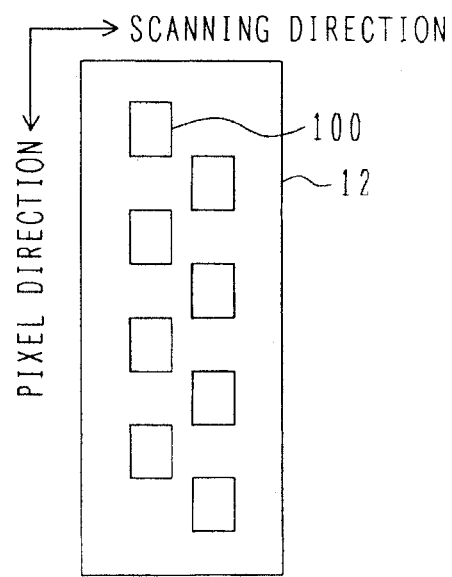
Figure 2C:
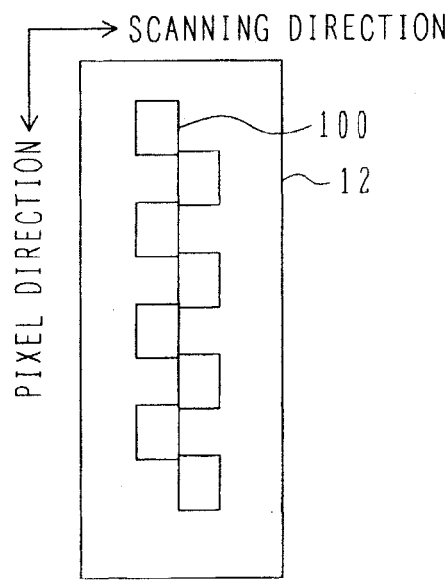

In an example shown in FIG. 2C, the image sensors 100 are arranged with no gaps between them in the scanning direction and in an overlapping manner in the pixel direction. In an example shown in FIG. 2D, the image sensors 100 are arranged with gaps between them in the scanning direction and in an overlapping manner in the pixel direction.

Figure 2D:
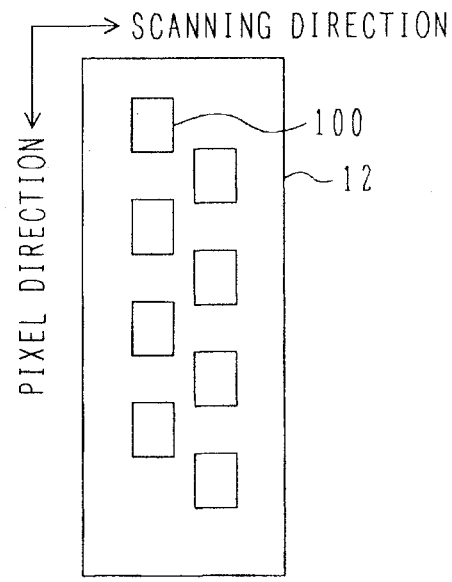

The example in FIG. 2B is advantageous over the example in FIG. 2A in that there is a mounting space, for instance, for a sensor cooling mechanism, a driver circuit, and an electron multiplier because the image sensors 100 are apart from each other. The examples in FIGS. 2C and 2D are advantageous over the examples in FIGS. 2A and 2B in that no pixels will fail in data acquisition even when the image sensors 100 are erroneously arranged in the pixel direction.

The detector 12 may be fabricated as a single image sensor die that is configured as shown in FIGS. 2A-2D or fabricated by arranging a plurality of sensor dies. The image sensor to be used may be a CCD (Charge Coupled Device) which is a one-dimensional line sensor, a TDI (Time Delay and Integration) image sensor, which is a time delay and integration, two-dimensional line sensor, or an electron multiplication line sensor.

From the viewpoint of a sensor structure, a front illuminated image sensor, a back illuminated image sensor, or an anti-blooming image sensor may be used. Further, only the image sensor to be used may be selected from the plurality of image sensors and driven. Furthermore, the plurality of image sensors may be multi-tap image sensors that are capable of parallel reading a plurality of units (taps) of several pixels, which are divided in pixel direction.

Moreover, the image sensor to be used may be an electron multiplication image sensor that provides electron multiplication at its former stage or latter stage.

FIGS. 3A to 3D show typical detector configurations that may be employed when area sensors are used with the defect inspection apparatus according to the present invention. As shown in FIGS. 3A to 3D, the detector 12 includes a plurality of image sensors 100. The plurality of image sensors 100 (four image sensors in the examples shown in the figures) are arranged at certain intervals in the pixel direction to form four lines. Further, the image sensors 100 are arranged so that they are not contiguous to each other in the scanning direction. In other words, the plurality of image sensors 100 are arranged in a lattice pattern.

Figure 3A:
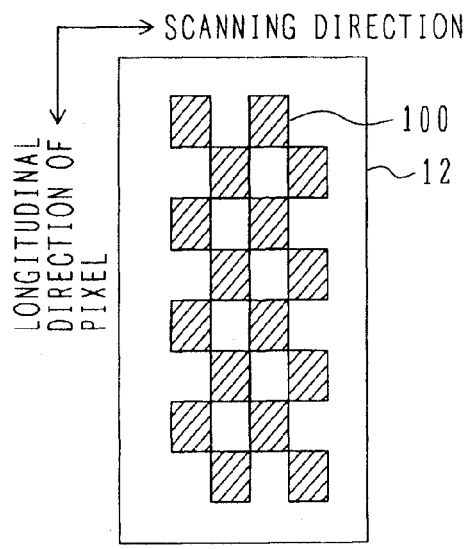
FIGS. 3A to 3D show typical detector configurations that may be employed when area sensors are used with the defect inspection apparatus according to the present invention.

In an arrangement example shown in FIG. 3A, the image sensors 100 are arranged with no gaps between them in both the longitudinal direction of pixel (pixel direction) and the scanning direction. In an arrangement example shown in FIG. 3B, the image sensors 100 are arranged with gaps between them in both the scanning direction and the longitudinal direction of pixel. In an arrangement example shown in FIG. 3C, the image sensors 100 are arranged with no gaps between them in the longitudinal direction of pixel and in an overlapping manner in the scanning direction. In an arrangement example shown in FIG. 3D, the image sensors 100 are arranged with no gaps between them in the scanning direction and in an overlapping manner in the longitudinal direction of pixel.

Figure 3B:
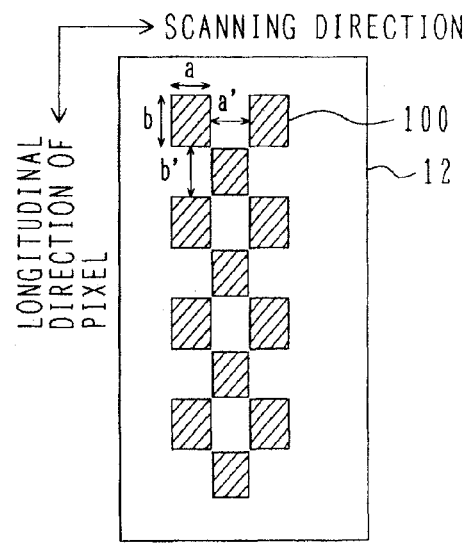
Figure 3C:
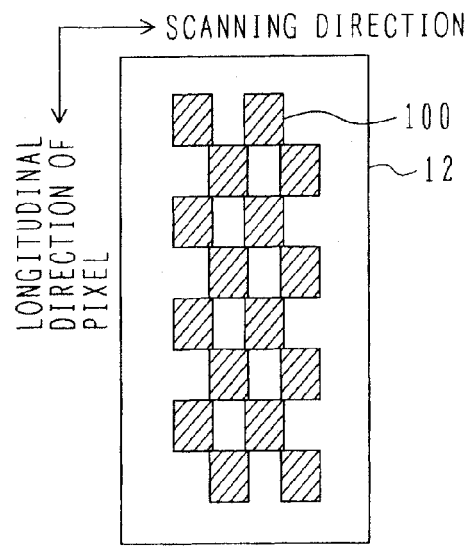
Figure 3D:
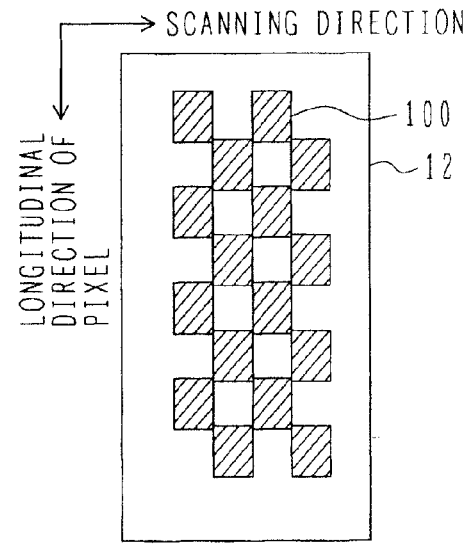

When, as shown in FIG. 3B, the dimension of an image sensor 100 in the scanning direction is a, the dimension of an image sensor 100 in the longitudinal direction of pixel is b, the interval between image sensors 100 in the scanning direction is a', and the interval between image sensors 100 in the longitudinal direction of pixel is b', a=0 and b=0 in the example shown in FIG. 3A.

In the example shown in FIG. 3B, a<a' and b<b'. In the example shown in FIG. 3C, a<a' and b=b'. In the example shown in FIG. 3D, a=a' and b<b'.

The image sensor to be used may be a CCD, which is a two-dimensional area sensor, or an electron multiplication area sensor. From the viewpoint of a sensor structure, a front illuminated image sensor, a back illuminated image sensor, or an anti-blooming image sensor may be used. When an area sensor is used, it acquires an image optically and inspects the inspection target for defects and the like by means of image processing or the like while the detector or the stage on which the inspection target is mounted is moved for scanning and stopped upon image acquisition.

Figure 4:
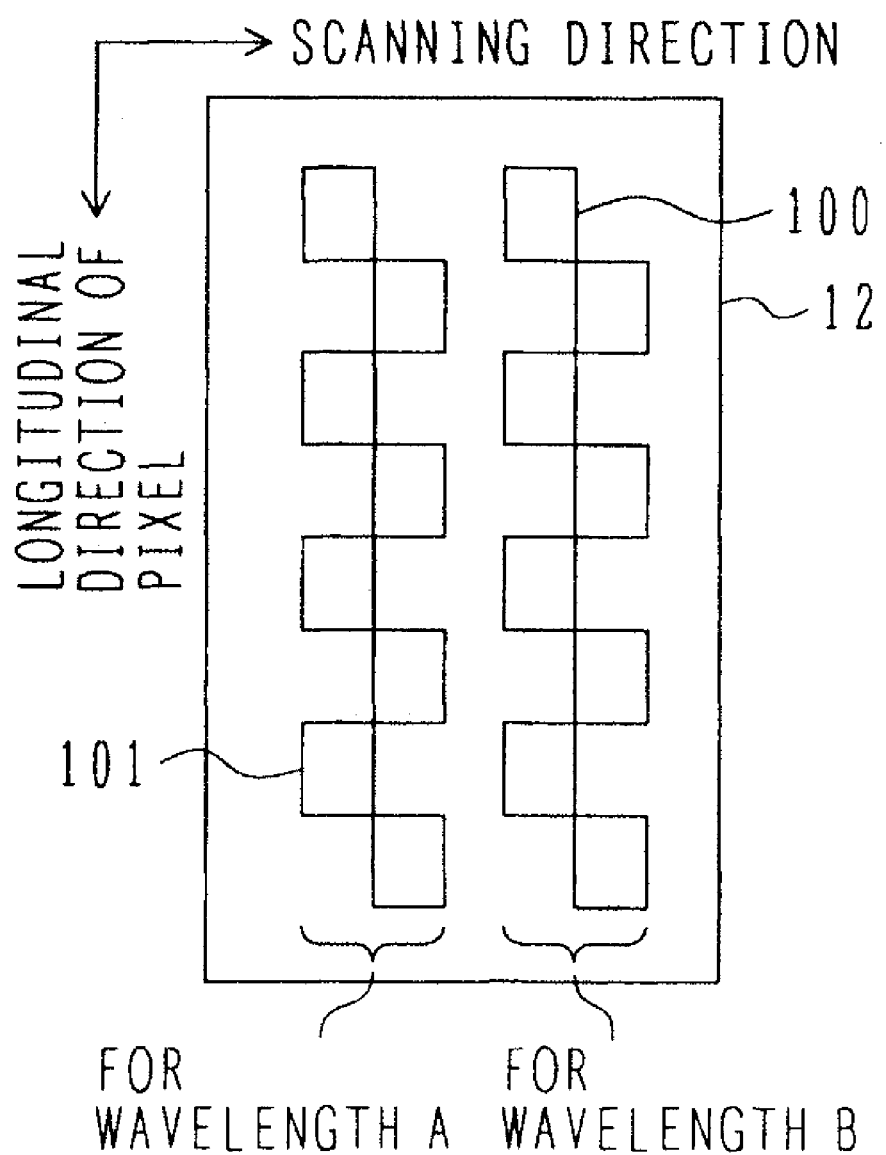
FIG. 4 shows a typical detector configuration in which image sensors having different spectral sensitivities are arranged in a lattice pattern to form a plurality of lines within the defect inspection apparatus according to the present invention.

FIG. 4 shows a typical detector configuration in which image sensors having different spectral sensitivities are arranged in a lattice pattern to form a plurality of lines within the defect inspection apparatus according to the present invention. The detector 12 includes two different image sensor arrangements. One is for wavelength A and the other is for wavelength B. In the wavelength A arrangement, image sensors 101 highly sensitive to wavelength A are arranged in a lattice pattern with no gaps between them in both the scanning direction and the longitudinal direction of pixel. In the wavelength B arrangement, image sensors 102 highly sensitive to wavelength B are arranged with no gaps between them in both the scanning direction and the longitudinal direction of pixel.

The above configuration makes it possible to provide a detector that is highly sensitive to different wavelengths (wavelengths A and B) and can be used with an inspection apparatus to perform high-speed inspection.

Although the present embodiment assumes that the image sensors are arranged for two different wavelengths (wavelengths A and B), the image sensors may be arranged for three or more different wavelengths. Further, the image sensors 101, 102 may be arranged with gaps between them or in an overlapping manner as indicated in FIGS. 2A-2D and 3A-3D.

Figure 5A:
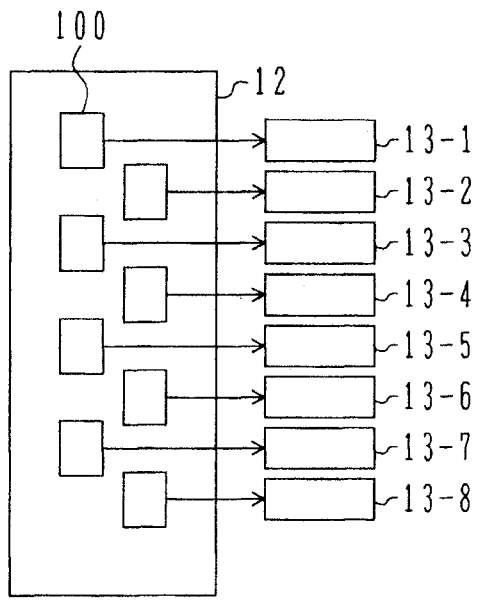
FIGS. 5A to 5C show typical configurations of image processing units for use with the defect inspection apparatus according to the present invention.
Figure 5B:
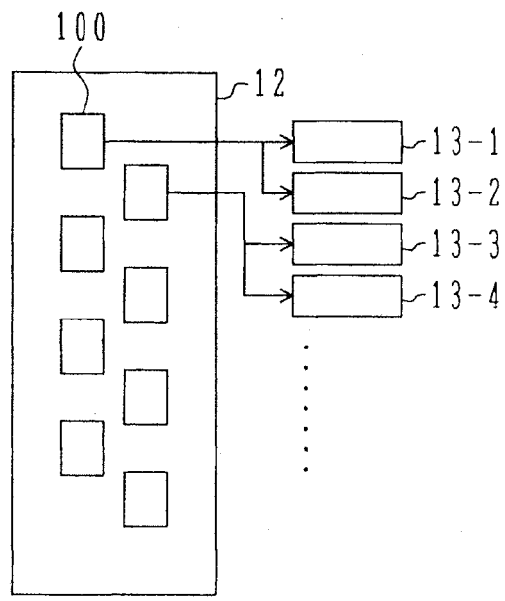
Figure 5C:
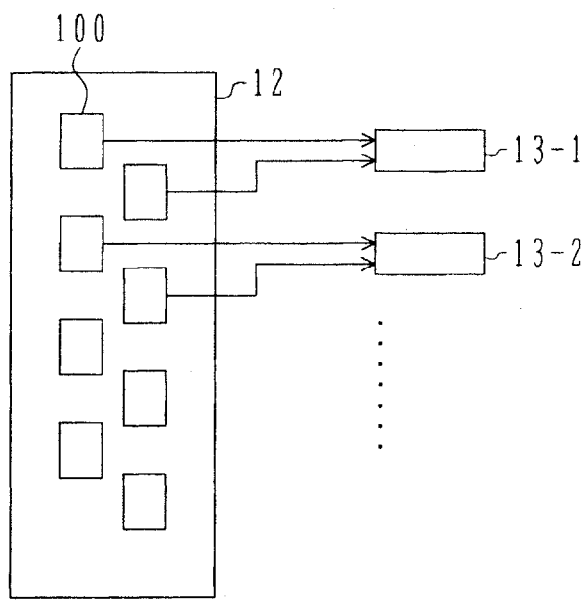

FIGS. 5A to 5C show typical configurations of the image processing units for use with the defect inspection apparatus according to the present invention. The image processing units 13 may be configured on a one-to-one basis with respect to the image sensors 100 as shown in FIG. 15A, on a one-to-N basis with respect to the image sensors 100 as shown in FIG. 15B, or on an N-to-one basis with respect to the image sensors 100 as shown in FIG. 15C. The image processing units 13-1, 13-2, 13-3, . . . parallel process signals output from the plurality of image sensors 100.

In the examples shown in FIGS. 5A to 5C, the image processing units 13-1, 13-2, 13-3, . . . may be interconnected in a manner not shown and used to perform an overlap process. In the example shown in FIG. 5A, for instance, image processing units 13-1 and 13-2 may be connected with a signal line to perform a synthesis process on an overlapping region of two image sensors 100 or perform a process, for instance, for selecting an output from either of the two image sensors 100.

FIGS. 6A and 6B show typical detector configurations in which image sensors having different sensitivities are arranged to form a plurality of lines within the defect inspection apparatus according to the present invention. As shown in FIG. 6a, the detector 12 includes two different image sensor arrangements. One is for high sensitivity and the other is for low sensitivity. In the high-sensitivity arrangement, an image sensor 103 having high sensitivity is used. In the low-sensitivity arrangement, an image sensor 104 having low sensitivity is used. This makes it possible to perform inspection over a wide dynamic range with one scan (inspection). Consequently, it is possible to provide an inspection apparatus that is capable of determining a wide variety of defect sizes in a situation where the inspection apparatus determines the sizes of defects detected by an image processing unit.

Alternatively, the image sensors having different sensitivities may be arranged as shown in FIG. 6B. More specifically, image sensors 103 and image sensors 104, which differ in sensitivity, may be arranged in a lattice pattern with no gaps between them in both the scanning direction and the longitudinal direction of pixel. The image sensors 103, 104 may also be arranged with gaps between them or in an overlapping manner as shown in FIGS. 2A-2D and 3A-3D.

Although the present embodiment assumes that image sensors having two different sensitivities are arranged, image sensors having three or more different sensitivities may alternatively be used. Further, the image sensor arrangements having different sensitivities may be accomplished by using the same image sensors and adjusting the amplifier gain or electron multiplier gain or by using image sensors having different sensitivities.

Figure 7:
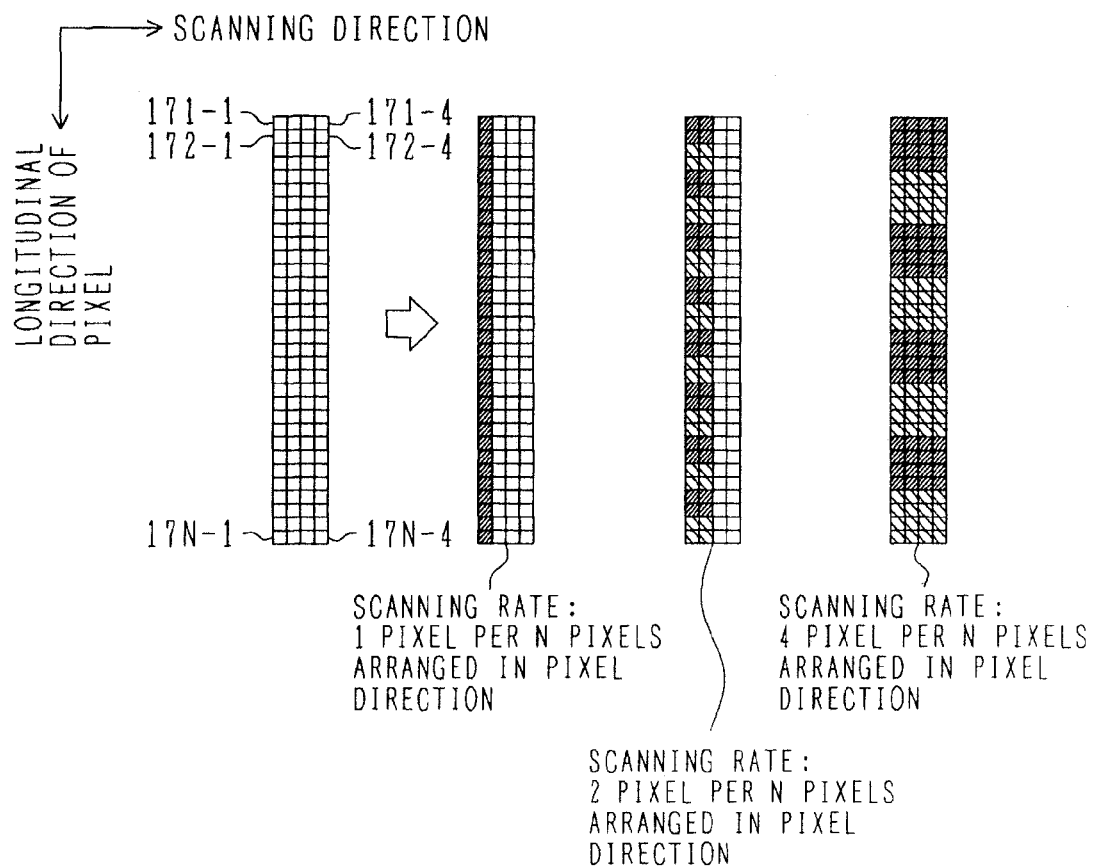
FIG. 7 shows a typical method of exercising resolution control by varying the number of available pixels of an image sensor in the defect inspection apparatus according to the present invention.

FIG. 7 shows a typical method of exercising resolution control by varying the number of available pixels of an image sensor in the defect inspection apparatus according to the present invention. As shown in FIG. 7, when a scanning rate is 1, the number of available pixels of an area sensor is 1 pixel in the scanning direction and N pixels in the pixel direction (pixels 171-1 to 17N-1) and the 1×1 pixel of the area sensor is used as one pixel. When the scanning rate is 2, the number of available pixels is 2 pixels in the scanning direction and N pixels in the pixel direction (pixels 171-1 to 17N-1 and 171-2 to 17N-2) and the 2×2 pixels of the area sensor are combined and used as one pixel ((171-1, 171-2, 172-1, 172-2), (173-1, 173-2, 174-1, 174-2), . . . ).

When the scanning rate is 4, the number of available pixels is 4 pixels in the scanning direction and N pixels in the pixel direction (pixels 171-1 to 17N-1, 171-2 to 17N-2, 171-3 to 17N-3, and 171-4 to 17N-4) and the 4×4 pixels of the area sensor are combined and used as one pixel ((171-1 to 171-4, 172-1 to 172-4, 173-1 to 173-4, 174-1 to 174-4), (175-1 to 175-4, 176-1 to 176-4, 177-1 to 177-4, 178-1 to 178-4, . . . ).

The process for combining the pixels (pixel output signal combination process) is performed by the image processing unit. This ensures that a detected image can be obtained at three different scanning rates (resolutions) with only one type of detection lens. Consequently, the defect inspection apparatus having three different resolutions can be provided at a lower cost than a defect inspection apparatus having three types of detection lens.

The present embodiment is configured so that an image sensor provides three different resolutions. Alternatively, however, the number of pixels in the scanning direction may be increased to provide four or more different resolutions.

The defect inspection apparatus according to the present invention, which has been configured described above, increases the number of detector pixels for inspection speed enhancement by arranging conventional image sensors in a lattice pattern. The present invention can provide a defect inspection apparatus capable of performing inspection at high speed because it can enlarge the detection field of view in the above manner.

Further, the defect inspection apparatus according to the present invention is configured so that image sensors having different sensitivities are arranged in the scanning direction. Therefore, the present invention provides a defect inspection apparatus that is highly sensitive to a plurality of wavelengths and provided with a wide dynamic range.

Furthermore, the defect inspection apparatus according to the present invention can change the combination of a plurality of pixels to select a plurality of different scanning rates. A detected image can therefore be obtained at a plurality of different scanning rates (resolutions) with only one type of detection lens. Consequently, a defect inspection apparatus having a plurality of different resolutions can be provided at a lower cost than a defect inspection apparatus having a plurality of types of detection lens.

The present invention not only provides the defect inspection apparatus but also a defect inspection method.

The defect inspection method for inspecting an inspection target illuminates the inspection target with illumination light, receives light reflected from the inspection target with a plurality of photoelectric image sensors, moves the inspection target, and inspects the inspection target in accordance with the reflected light, which is detected by the plurality of photoelectric image sensors. The defect inspection method causes the photoelectric image sensors to detect the light reflected from the inspection target at fixed intervals relative to a single line direction region in a direction perpendicular to a direction in which the inspection target moves, and later detects light reflected from a region within the single line direction region of the inspection target from which no reflected light has been detected.

The aforementioned fixed intervals may be substantially equal to a dimension of one of the photoelectric image sensors in a direction substantially perpendicular to the direction in which the inspection target moves.

What is claimed is:

1. A defect inspection apparatus comprising:
    illumination unit for illuminating an inspection target with illumination light;
    a detector that has photoelectric image sensors to receive light reflected from the inspection target;
    a transport unit for transporting the detector or a stage on which the inspection target is mounted; and
    an inspection unit for inspecting the inspection target in accordance with an image detected by the detector,
    wherein the plurality of photoelectric image sensors are alternately arranged in each of two or more lines to form a lattice-like pattern, and the plurality of photoelectric image sensors are spaced apart from each other to provide a mounting space, and at least one of a sensor cooling mechanism, a driver circuit, and an electron multiplier is arranged in said mounting space.

2. The defect inspection apparatus according to claim 1, wherein the plurality of photoelectric image sensors arranged in a lattice pattern have a spectral sensitivity that varies from one line to another; and wherein the illumination unit includes a light source having a plurality of wavelengths or a plurality of light sources that differ in wavelength.

3. The defect inspection apparatus according to claim 1, wherein the photoelectric image sensors are two-dimensional area sensors that acquire an image optically and inspect a defect of the inspection target by means of image processing while the detector or the stage on which the inspection target is mounted is moved for scanning and stopped upon image acquisition.

4. The defect inspection apparatus according to claim 1, further comprising:
    a sensitivity control unit for adjusting sensitivities of the plurality of photoelectric image sensors.

5. The defect inspection apparatus according to claim 1, wherein the photoelectric image sensors are time delay and integration image sensors.

6. The defect inspection apparatus according to claim 5, wherein the time delay and integration image sensors are anti-blooming TDI image sensors.

7. The defect inspection apparatus according to claim 5, wherein the time delay and integration image sensors are back surface radiation TDI image sensors.

8. The defect inspection apparatus according to claim 5, wherein the time delay and integration (TDI) image sensors are multi-tap image sensors that are capable of parallel reading a plurality of units of several pixels, which are divided in pixel direction.

9. The defect inspection apparatus according to claim 1, wherein the image sensors are electron multiplication image sensors that provide electron multiplication at a former stage or a latter stage.

10. The defect inspection apparatus according to claim 1, further comprising:
    image processing units the number of which is an integer multiple of the number of the plurality of image sensors, wherein the image processing units parallel process output signals generated from the plurality of image sensors.

11. The defect inspection apparatus according to claim 1, further comprising:
    image processing units the number of which is a real number multiple of the number of the plurality of image sensors, wherein the image processing units parallel process output signals generated from the plurality of image sensors.

12. The defect inspection apparatus according to claim 3, further comprising:
    image processing units that can exercise variable control over pixels available from a plurality of pixels of the two-dimensional area sensors.

13. The defect inspection apparatus according to claim 12, wherein the image processing units, the number of which is a real number multiple of the plurality of image sensors, parallel process output signals generated from the available pixels.

14. A defect detector that is used in a defect inspection apparatus and includes photoelectric image sensors to receive light reflected from an inspection target, the defect detector comprising:
    a plurality of photoelectric image sensors, which are alternately arranged in each of two or more lines to form a lattice-like pattern,
    wherein the plurality of photoelectric image sensors are spaced apart from each other to provide a mounting space, and at least one of a sensor cooling mechanism, a driver circuit, and an electron multiplier is arranged in said mounting space.

15. The defect detector according to claim 14, wherein the plurality of photoelectric image sensors alternately arranged in two or more lines are arranged in a direction perpendicular to a direction of scanning the inspection target; and
    wherein the two or more lines of photoelectric image sensors are arranged in the direction of scanning the inspection target.

16. The defect detector according to claim 15, wherein, when the length of a photoelectric image sensor in the scanning direction is a, the length of a photoelectric image sensor in a direction perpendicular to the scanning direction is b, the interval between the photoelectric image sensors in the scanning direction is a', and the interval between the photoelectric image sensors in a direction perpendicular to the scanning direction is b', a =a' and b =b'.

17. The defect detector according to claim 15, wherein, when the length of a photoelectric image sensor in the scanning direction is a, the length of a photoelectric image sensor in a direction perpendicular to the scanning direction is b, the interval between the photoelectric image sensors in the scanning direction is a', and the interval between the photoelectric image sensors in a direction perpendicular to the scanning direction is b', a <a' and b<b'.

18. The defect detector according to claim 15, wherein, when the length of a photoelectric image sensor in the scanning direction is a, the length of a photoelectric image sensor in a direction perpendicular to the scanning direction is b, the interval between the photoelectric image sensors in the scanning direction is a', and the interval between the photoelectric image sensors in a direction perpendicular to the scanning direction is b', a >a' and b=b'.

19. The defect detector according to claim 15, wherein, when the length of a photoelectric image sensor in the scanning direction is a, the length of a photoelectric image sensor in a direction perpendicular to the scanning direction is b, the interval between the photoelectric image sensors in the scanning direction is a', and the interval between the photoelectric image sensors in a direction perpendicular to the scanning direction is b', a =a' and b>b'.

20. The defect detector according to claim 15, wherein variable control is exercised over pixels available from a plurality of pixels of the photoelectric image sensors to select a plurality of scanning rates.

* * * * *